United States Patent [19]

Khokhar et al.

[11] Patent Number: 5,041,581

[45] Date of Patent: Aug. 20, 1991

[54] HYDROPHOBIC CIS-PLATINUM COMPLEXES EFFICIENTLY INCORPORATED INTO LIPOSOMES

[75] Inventors: Abdul R. Khokhar; Gabriel Lopez-Berestein; Roman Perez-Soler, all of Harris, Tex.

[73] Assignee: The University of Texas System Board of Regents, Austin, Tex.

[21] Appl. No.: 914,591

[22] Filed: Oct. 7, 1986

Related U.S. Application Data

[63] Continuation-in-part of Ser. No. 788,750, Oct. 18, 1985.

[51] Int. Cl.$^5$ .................................... C07F 15/00
[52] U.S. Cl. ................................. 556/137; 260/414; 514/492
[58] Field of Search .................................. 556/137

[56] References Cited

U.S. PATENT DOCUMENTS

| | | | |
|---|---|---|---|
| 3,904,663 | 9/1975 | Tobe | 556/136 |
| 3,993,754 | 11/1976 | Rahman | 556/136 X |
| 4,115,418 | 9/1978 | Gale et al. | 556/137 |
| 4,137,248 | 1/1979 | Gale et al. | 556/137 |
| 4,140,707 | 2/1979 | Cleare | 556/136 |
| 4,169,846 | 10/1979 | Kidani | 556/136 |
| 4,203,912 | 5/1980 | Hydes et al. | 556/137 |
| 4,225,529 | 9/1980 | Hydes et al. | 556/137 |
| 4,230,631 | 10/1980 | Hydes et al. | 556/137 |
| 4,241,046 | 12/1980 | Papahadjopoulos | 556/136 |
| 4,271,085 | 6/1981 | Amundsen et al. | 556/137 |
| 4,431,666 | 2/1984 | Bulten | 556/136 |
| 4,466,924 | 8/1984 | Verbeek | 556/136 |
| 4,657,927 | 4/1987 | Cleare | 556/136 |
| 4,661,516 | 4/1987 | Brown et al. | 556/137 X |
| 4,663,167 | 5/1987 | Lopez-Berestein | 556/136 X |
| 4,680,308 | 7/1987 | Schwartz | 556/136 |
| 4,760,155 | 7/1988 | Heffernan | 556/136 |
| 4,760,156 | 7/1988 | Heffernan | 556/136 |
| 4,760,157 | 7/1988 | Child | 556/136 |

FOREIGN PATENT DOCUMENTS

| | | | |
|---|---|---|---|
| 569425 | 12/1985 | Australia | 556/137 |
| 898614 | 1/1984 | Belgium | 556/136 |
| 113508 | 4/1983 | European Pat. Off. | 556/137 |
| 130482 | 2/1984 | European Pat. Off. | 556/137 |
| 136012 | 3/1984 | European Pat. Off. | 556/137 |
| 198765 | 4/1986 | European Pat. Off. | 556/136 |
| 193936 | 5/1986 | European Pat. Off. | 556/137 |

OTHER PUBLICATIONS

Ridgway et al., J. Clin Hematol. Oncol. vol. 7(1); pp. 220-230 (1977).
Speer et al., J. Clin. Hematol. Oncol., vol. 7(3) p. 856 (1977).
Schwartz et al., Cancer Treatment Reports, 61:1519-1525 (1977).
Chemical Abstracts 93 125661, 125662 (1980).
Chemical Abstracts 103 226307n, 226308p (1985).
Chemical Abstracts 105 126821y (1986).
Chemical Abstracts 101 182656c (1984.
Chemical Abstracts 84 54030n (1976).
Chemical Abstracts 88 570c (1978).
Chemical Abstracts 94 218774t (1981).
Connors et al., Chem. Biol. Interactions, vol. 5 p. 419 (1972).
Chemical Abstracts 101:177510w.
Maeda et al., Japan Journal Cancer Research (Gann), 77:523-525 (Jun. 1986).
Perez-Soler, Cancer Research 46:6269-6273 (1986).

*Primary Examiner*—Paul F. Shaver
*Attorney, Agent, or Firm*—Arnold, White & Durkee

[57] ABSTRACT

The present invention involves the synthesis and use of new platinum compounds. These new platinum compounds are easy to encapsulate in liposomes at high efficiencies. They are further characterized as platinum (II) four coordinate complex having the formula:

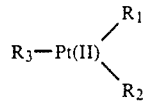

wherein $R_1$ and $R_2$ *are carboxylato monoanions bearing a hydrophobic radical function or a single carboxylato dianion bearing a hydrophobic radical function and* $R_3$ is a vicinal diaminoalkane or vicinal diaminocycloalkane. The complex is substantially soluble in methanol or chloroform and substantially insoluble in water. Said complex may be incorporated into phospholipid liposomes. Such platinum complexes encapsulated in phospholipid liposomes are useful for chemotherapy of platinum complex-sensitive tumors.

40 Claims, No Drawings

HYDROPHOBIC CIS-PLATINUM COMPLEXES EFFICIENTLY INCORPORATED INTO LIPOSOMES

This is a continuation-in-part of U.S. patent application Ser. No. 788,750 filed Oct. 18, 1985.

BACKGROUND OF THE INVENTION

This invention relates to newly synthesized platinum complexes with hydrophobic properties. The use of liposomes incorporating these new and previously synthesized complexes in anti-tumor chemotherapy is also described.

Cis-platinum (CDDP) is a highly effective drug in the treatment of several neoplastic diseases in humans (Loehrer et al (1984) Ann. Int. Med. V 100, pp 704–713). However, its use is limited by severe systemic toxicity, particularly nephrotoxicity and neurotoxicity (Zwelling et al Platinum Complexes. In: Pharmacologic principles of cancer treatment (1982) Ed by B. A. Chabner, Saunders, Philadelphia, PA). In an attempt to modify the therapeutic index of CDDP, new derivatives have been synthesized during the last decade. However, the development of some promising analogs has been prevented by their low hydrosolubility, which decreases their potential for clinical use (Burchenal et al (1979) Cancer Treat. Rep. V 63, pp 1493–1497).

Liposomes are lipid vesicles which may form spontaneously upon addition of an aqueous solution to a dry lipid film (Mayhew et al, In: Liposomes (1983) Ed by Marc J. Ostro, Marcel Dekker, Inc., New York, N.Y.). Liposomes may be used as drug carriers of hydrophobic or hydrophilic drugs entrapped in their hydrophobic or hydrophilic compartments respectively. Multilamellar liposomes are multilayer lipid vesicles (MLV) that are particularly suited for carrying hydrophobic drugs since their hydrophobic compartment is larger than their hydrophilic compartment. When injected intravenously (iv) in animals, (Kasi et al (1984) Int. J. Nucl. Med. Biol. V 11 pp 35–37, Lopez-Berestein et al. (1)(1984) Cancer Drug Deliv. V 1, pp 199–205) and humans (Lopez-Berestein et al (2)(1984), Cancer Res. V 44, pp 375–378), MLV concentrate in the liver, spleen and other organs rich in reticuloendothelial (RES) cells.

Liposomes have been previously used in vitro to deliver chemotherapeutic agents, (Mayhew et al, Liposomes (1983), Ed by Ostro, Marcel Dekker, Inc., New York, N.Y.) and immunomodulators and anti-fungal agents in vitro (Mehta et al (1984), Immunology V51 pp 517–527, and in vivo in animals (Lopez-Berestein et al (4)(1984) Clin Exp Metastasis V 2 pp 127–137 and Lopez-Berestein et al (1983), J Inf Dis V 147, pp 937–945) and in humans (Lopez-Berestein et al (1985) J. Inf. Dis. V 151 pp 704–710).

Recent studies show that liposomes can reduce certain types of drug-related toxicities such as doxorubicin cardiotoxicity (Forssen et al (1981) Proc. Natl. Acad. Sci. V 78 pp 1873–1877, Olson et al (1982), Eur. J. Cancer Clin. Oncol. V 18 pp 167–176, Gabizon et al (1982) Cancer Res. V 42 pp 4734–4739, Herman et al (1983) Cancer Res. V 43 pp 5427–5432) and CDDP nephrotoxicity, (Freise et al (1982), Arch. Int. Pharmacodynamie Therapie V 258 pp 180–192) and may increase antitumor activity as a result of a slow release mechanism (Mayhew et al (1978) Ann. N.Y. Acad. Sci. V 308, pp 371–386, Patel et al (1984) Int. J. Cancer V 34 pp 717–723) a higher drug uptake by tumor cells or due to a more selective organ distribution (Gabizon et al (1983) Cancer Res. V 43, pp 4730–4735 and Mayhew et al (1983), Cancer Drug Deliv. V 1 pp 43–58). In U.S. Pat. No. 4,330,534 $N^4$-acylcytosine arabinoside incorporated into liposomes, for example, was found to therapeutically effective when administered to tumor-bearing animals. In spite of these promising results, the clinical application of antitumor agents encapsulated in liposomes has been delayed, mainly due to formulation, drug stability and large scale production problems.

CDDP has been previously encapsulated in MLV but with a very low encapsulation efficiency (7.4%) and poor stability (75% at 48 hours in 0.9% NaCl solution) (Freise et al (1982) Arch. Int. Pharmacodynamie Therapie V 258 pp 180–192).

In U.S. Pat. No. 4,256,652 are described certain platinum compounds comprising resolved stereoisomers of 1,2 diaminocyclohexane (DACH). The isomers utilized were cis-DACH, trans-RR-DACH and trans-SS-DACH. The platinum compounds described therein contained, in addition to a resolved DACH isomer, two hydrophilic platinum ligands such as bromide, iodide, nitrate, bromoacetate, sulfate or glucuronate. The platinum compounds comprising the trans-RR-DACH were described as often more therapeutically effective than those bearing cis-DACH.

In European Patent Application No. 83306726.7 certain platinum compounds are described which may comprise diaminocyclohexane (non-stereochemically resolved) and do comprise phosphatidyl groups having fatty acid substituents. These compounds are described as largely insoluble in plasma and preferably employed with lipid vesicle carriers. The platinum compound-phospholipid vesicles were preferably prepared by a sonic oscillation procedure which characteristically yields unilamellar vesicles.

SUMMARY OF THE INVENTION

The present invention comprises a platinum (II) four-coordinate complex having the formula:

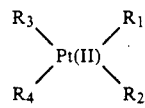

In this formula $R_1$ and $R_2$ are each carboxylates bearing a hydrophobic radical function, most preferably neodecyl, or, when linked together, are a dicarboxylato bearing a hydrophobic radical function. The $R_3$ and $R_4$ are each:

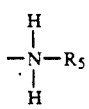

In this latter formula, $R_5$ is selected from the group consisting of hydrogen, an alkyl having from 2 to 6 carbon atoms such as isopropyl, aryl, aralkyl, alkenyl, a cycloalkyl such as cyclohexyl, cycloalkenyl and a combination thereof $R_5$ is preferably hydrogen, alkyl having between 1 and 20 carbon atoms, more preferably between 6 and 12 carbon atoms and most preferably between and 6 carbon atoms or cycloalkyl having between 3 and 12 carbon atoms.

Additionally $R_3$ and $R_4$ may be linked together in a single function. When $R_3$ and $R_4$ are so linked together, they are preferably selected from the group consisting of cycloalkyl-1,2-diamino functions having between about 3 and 7 carbon atoms, and alkyl-1,2-diamino having between about 2 and 12 carbon atoms, preferably ethyl. A preferred cycloalkyl-1,2-diamino component is 1,2-diaminocyclohexane, preferably in the trans-R,R- or trans-S,S- form.

In the above-described complex the carboxylato of $R_1$ and $R_2$ is preferably an alkylcarboxylato having between about 5 and 20 carbon atoms, an arylcarboxylato wherein aryl is phenyl, naphthyl, or an alkylphenyl wherein the alkyl phenyl has between about 12 and 16 carbon atoms.

When the complex contains $R_1$ and $R_2$ as a dicarboxylato, the dicarboxylato is preferably an alkyldicarboxylato having between about 5 and 20 carbon atoms, or an aryldicarboxylato wherein aryl is naphthyl, phenyl, or alkylphenyl wherein the alkyl of the alkylphenyl has between about 6 and 12 carbon atoms. As used in the above description the term aryl is defined further as a function preferably having between about 6 and 14 carbon atoms. Likewise the term alkenyl is preferably a function having between about 5 and 20 carbon atoms.

The cycloalkyl referred to in the present descriptions is preferably a function having between about 3 and 12 carbon atoms. The cycloalkenyl term as used above is preferably a function having between about 5 and 20 carbon atoms. The term aralkyl as used above is a function preferably having between about 7 and 20 carbon atoms and contains linked aryl and alkyl portions. The aryl portion herein preferably has between about 6 and 10 carbon atoms and the alkyl portion preferably has between about 1 and 10 carbon atoms. When $R_3$ and $R_4$ are taken together they are preferably a cycloalkyl-1,2-diamino having between about 3 and 20 carbon atoms. The alkyl ring of the cycloalkyl preferably has between about 3 and carbon atoms.

A further aspect of the present invention concerning the platinum (II) four-coordinate complex having the formula:

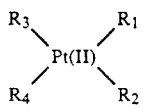

concerns the case where $R_1$ and $R_2$, taken tog dicarboxylato, preferably a cis dicarboxylato, of the formula:

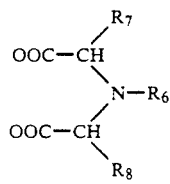

where $R_6$ is alkyl having between about 10 and 20 carbon atoms, preferably pentyl, neopentyl, decyl or neodecyl and $R_7$ and $R_8$ are each hydrogen or an alkyl having between about 1 and 5 carbon atoms.

As described above $R_3$ and $R_4$ are each:

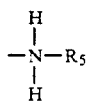

When $R_3$ and $R_4$ are taken together they are selected from the group consisting of cycloalkyl-1,2-diamino having between about 3 and 7 carbon atoms, and alkyl-1,2-diamino having between about 2 and 12 carbon atoms. The cycloalkyl-1,2-diamino is preferably 1,2-diaminocyclohexane and more preferably trans-R,R-1,2-diaminocyclohexane or trans-S,S-1,2-diaminocyclohexane. This complex is, as described above, substantially soluble in methanol or chloroform and substantially insoluble in water.

Important aspects of the present invention involve liposomes comprising fatty substances such as phospholipids, optionally cholesterol, and the four-coordinate platinum complexes described above, as well as the preparation and uses of these liposomes. Liposomes of the present invention contain the platinum complex and the phospholipid in a preferred ratio between about 1 to 10 and about 1 to 30, a more preferred ratio being 1 to 15.

Preferred phospholipids of these liposomes include phosphatidylglycerol, phosphatidylcholine, sphingomyelin, phosphatidic acid or phosphatidylserine, the more preferred phospholipids being phosphatidylglycerol, phosphatidylcholine or a combination thereof. The most preferred phosphatidylglycerol is one consisting essentially of dimyristoylphosphatidylglycerol and the most preferred phosphatidylcholine is one consisting essentially of dimyristoylphosphatidylcholine. When the liposomes of the present invention comprise dimyristoylphosphatidylglycerol and dimyristoylphosphatidylcholine they are preferably in a ratio between about 1-10 and 10-1, more preferably in a ratio of about 3 to 7.

The liposomes of the present invention may be multilamellar, unilamellar or have an undefined lamellar construction. A pharmaceutical composition comprising the liposomes of and a pharmaceutically acceptable carrier or diluent may be used for the therapy of disease conditions such as cancer.

A focal point of the present invention involves a method of treating a host animal afflicted with tumor cells sensitive to the presence of a platinum (II) four-coordinate complex. This method comprises administering to the host an amount of the platinum (II) four-coordinate complex described above or a liposome of the present invention comprising a phospholipid and a tumor cell-inhibiting effective amount of said platinum complex. The administering step is preferably parenteral and by intravenous, intraarterial, intramuscular, intralymphatic, intraperitoneal, subcutaneous, intrapleural or intrathecal injection or by topical application or oral dosage. Such administration is preferably repeated on a timed schedule, for example twice daily for a period of two weeks. The treatment may be maintained until tumor regression or disappearance has been achieved and may be used in conjunction with other forms of tumor therapy such as surgery or chemotherapy with different agents.

These antitumor methods may also be used to inhibit the metastatic spread of tumors such as reticulosarcoma. A preventative pretreatment with the platinum- (II) complexes or liposomes comprising those complexes may be used to preclude metastatic spread in a vaccination-like manner.

DETAILED DESCRIPTION OF PREFERRED EMBODIMENTS

Platinum (II) four-coordinate complexes were prepared utilizing racemic (unresolved) DACH, trans-RR-DACH or trans-SS-DACH. It was found that platinum complexes comprising trans-RR-DACH or trans-SS-DACH and two hydrophobic ligands such as cyclopentene-carboxylato were more efficiently incorporated into liposomes than were the analogous complexes comprising racemic DACH.

Liposomes incorporating these platinum complexes were found to be stable in an aqueous milieu, non-nephrotoxic and active against murine leukemia L-1210.

In a general sense, the square-planar platinum (II) four coordinate complexes of the present invention have the formula:

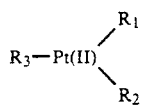

where $R_1$ and $R_2$ are preferably carboxylato monoanions bearing a hydrophobic radical function. $R_1$ and $R_2$ may also be a single carboxylato dianion where the carboxylato groups are bound to an interlinking atom which in turn is bound to a radical function. Additionally, $R_3$ is a vicinal diaminoalkane or vicinal diaminocycloalkane. It is contemplated that $R_3$ may be composed of two independent alkylamines, cycloalkylamines or ammonia. These components confer upon the complex a substantial solubility (normally greater than about 5.0 mg/ml) in methanol or chloroform at ambient temperatures and a substantial insolubility (less than about 0.5 mg/ml) in aqueous solutions at ambient temperatures.

The hydrophobic radical function, that function covalently pendant from the carboxyl group or from an intermediate or linking group, may be an alkyl, substituted aryl, aryl, alkenyl, cycloalkyl or cycloalkenyl group or even combinations of these functions such as alkylaryl or arylalkenyl, to name but two of the many possible hydrophobic combinations. The hydrophobic radical function characteristically has between 5 and 20 carbon atoms. When this hydrophobic radical function comprises an alkyl or alkenyl group, this group may be straight or branched. Polar functions such as hydroxyl groups, for example, substituted on the hydrophobic radicals would tend to lessen their hydrophobicity and may render them less useful for the purposes of the present invention.

In certain cases the $R_1$ and $R_2$ functions may be interlinked, for example when two acetate or propionate functions are bound together by a nitrogen atom. In these cases the $R_1$ and $R_2$ functions are a single carboxylato dianion. An alkyl hydrophobic function having between six and twenty carbon atoms, such as n-decane, for example, may be bound to the interlinking nitrogen and the resultant compound utilized in the production of the platinum (II) four coordinate complex of the present invention.

With certain hydrophobic radical functions (cyclopentene, for example) present on the carboxylato monoanion it was found that efficient incorporation of PT complexes into phospholipid liposomes was dependent on characteristics of the $R_3$ function. For example, when $R_3$ was 1, 2 diaminocyclohexane (DACH) the amino groups may be in several relative stereochemical configurations, cis, trans-RR and trans-SS (a mixture of these being termed "racemic"). With platinum (II) complexes containing cyclopentene radical functions ($R_1$ and $R_2$) and various stereochemical types of DACH it was found that the trans-RR-DACH and trans-SS-DACH-complexes were more efficiently incorporated into phospholipid liposomes (vesicles being a term equivalent to liposomes) than were the analogous racemic DACH complexes.

When a hydrophobic radical function was a branched alkyl containing nine carbon atoms such as that in neodecanoato, ($C_{10}H_{20}O_2$, empirical formula) the incorporation efficiency of a platinum (II) complex comprising racemic DACH or trans-RR-DACH was maximal (100%) Thus, linear or branched alkyl radical functions having from about 6 to about 12 carbon atoms confer properties of efficient phospholipid liposome incorporation upon any DACH-containing Pt (II) complex.

Liposomes containing the platinum (II) complexes described herein may be prepared from various amphipathic substances including natural or synthetic phospholipids. The phospholipids usable to produce liposomes are numerous and not exhaustively listed herein since they are generally well known in the art. These phospholipids include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides. Most preferable phospholipids for the practice of aspects of the present invention include dimyristoylphosphatidylglycerol (DMPG) and dimyristoylphosphatidylcholine (DMPC). Cholesterol in minor proportions ranging from less than 1% to about 50% may be included with phospholipids and platinum (II) complexes to produce liposomes of the present invention. A preferable but not limiting combination of DMPG and DMPC has been found to be a ratio of 3 to 7 although ratios between 1:10 and 10:1 are contemplated as satisfactory Ratios of platinum (II) complex to phospholipid between about 1 to 10 and about 1 to 30 are contemplated as generally satisfactory although a 1 to 15 ratio was primarily used in studies thus far.

Either unilamellar or multilamellar or other platinum (II) complex—containing liposomes may be used in the practice of the present invention. Multilamellar liposomes are presently preferred since the platinum (II) complexes of the present invention are substantially water —insoluble and they appear to be incorporated into the phospholipid bilayers of the liposome lamellae.

Generally, the procedure for synthesis of the platinum II compounds of the present invention may be described on one scale as follows: (1) about 10 mmole vicinal diamino cycloalkane or alkene are added to 50 ml aqueous solution of $K_2PtCl_4$ (3.5 g) and stirred for six to eight hours at room temperature. The yellow solid formed comprising cis-bis-dichloro-1,2-diamine-Pt(II) may be removed by filtration and washed with fluids such as water, methanol or acetone. The solid may then be suspended in about 20 ml $H_2O$ and an aqueous solution containing about 0.75 g $Ag_2SO_4$ added thereto. After stirring for about 24 hours in the dark, precipitated Ag Cl may be removed by filtration. The sulfato-vicinal diamine-Pt may then be dissolved in about 100 ml H₂O and added to about 2 m mol of alkali earth metal salt of a carboxylato anion prepared in situ, and stirred therewith for about 30 minutes. After removal of BaSO₄ by filtration, the platinum II complex of the present invention may be obtained, for example by crystallization or removal of the solvent by evaporation.

The methods of preparation of particular platinum (II) complexes and chemotherapeutic treatment with particular platinum (II) complexes described in the Examples contained later herein are readily adapted to the production and use of analogously described and claimed complexes by simple substitutions of appropriate vicinal diamines or hydrophobic radical-containing carboxylato monoanions.

Liposomes comprising phospholipids and platinum complexes (Pt-liposomes) of the present invention are useful in inhibiting both the growth and metastatic spread of tumors.

Such Pt-liposomes may be administered parenterally, topically or orally. Oral or parenteral dosages of these Pt-liposomes between about 2.5 mg/kg body weight and 25 mg/kg body weight are contemplated as adequate in most conditions. The particular dosages, if a tumor-bearing human is being treated may vary in each case according to the condition of the patient, the type and extent of tumor, and particular Pt-liposome toxicity.

The amount of liposomal-platinum included in the pharmaceutical composition and the dosage utilized in the method of treatment of the invention will vary depending in each case upon the conditions of the patients, the nature of the tumor undergoing treatment, antitumor activity of liposomal-platinum, the toxicity and solubility characteristics thereof, etc. Liposomal-platinum may also be administered in combination with other antitumor agents in a combined therapeutic regimen.

Parenteral administration may be intraperitoneal, subcutaneous, intrapleural, intrathecal, intraurethral, intravenous, intraarterial, intramuscular or intralymphatic. Such parenteral administration preferably involves Pt-liposome suspensions in pharmaceutically acceptable solutions such as sterile isotonic aqueous solutions. These suspensions may be obtained fully prepared or may be prepared from preformed components. As known to those skilled in the art, Pt-liposomes may be prepared as pellets or powders. These pellets or powders may be mixed with pharmaceutically acceptable solutions to form suspensions for parenteral administration.

Topical administration of Pt-liposomes may involve pharmaceutical compositions such as suspensions, creams or ointments which may be obtained fully prepared or prepared from Pt-liposome powders or pellets. Such topical administration may be near to sites of cancerous lesions such as the epithelium or mucosa for example.

Oral administrations of Pt-liposomes preferably involve encapsulation of Pt-liposome powder or pellets whereby the Pt-liposomes are protected from much gastric and intestinal digestive activity before release from the encapsulation.

When desired, Pt-liposomes may be prepared to contain, for example, other therapeutic agents for treatment of tumors or anti-oxidants to aid in liposome stabilization.

Use of the complexes of the present invention, particularly as a component of liposomes, focuses upon the inhibition of tumor growth and prevention of the metastatic spread of tumors. For example, first a host is identified as bearing a tumor type known to generally contain cells whose growth is often inhibited by platinum (II) complexes. Tumor growth in the host may be inhibited by administering to the host the PT-containing liposomes of the present invention.

Similarly, the metastatic spread of tumors in a host may be inhibited. A host bearing metastatic or potentially metastatic tumors of a type noted often to be sensitive to platinum (II) complexes, would first be identified. The administration of the PT-containing liposomes of the present invention to that host would serve to inhibit metastatic spread.

The following examples are presented to further illustrate preferred embodiments of the present invention; they are not intended to limit the invention unless otherwise so stated in the accompanying claims.

EXAMPLE 1

Materials and Analyses

K₂PtCl₄ was purchased from AESAR (Johnson Matthey, Inc. Seabrook, NH). Cyclopentenecarboxylic acid was purchased from Pfaltz and Bauer, Inc., Stamford, CT; 1,2-diaminocyclohexane (DACH) from Aldrich Chemical Co., Milwaukee, WI., trans-RR-DACH and trans-SS-DACH from Mortol Thiokol, Inc., Danvers, MO., and neodecanoic acid from Exxon Chemical Co., Houston, Texas. Elemental analyses on the platinum complexes were performed by Integral Microanalytical Laboratories, Inc., Raleigh, NC and by Robertson Laboratory, Inc., Florham Park, N.J. Infrared spectra of the complexes (as KBr pellets) were measured in the range of 600-4000 cm⁻¹ using a Nicolet 6000 Fourier transform infrared spectrophotometer.

Chromatographically pure (thin-layer chromatography) dimyristoylphosphatidylcholine (DMPC) and dimyristoylphosphatidylglycerol (DMPG) used in this study were obtained from Avanti Polar Lipids (Birmingham, AL). Cholesterol was purchased from Sigma Chemical Co. (St. Louis, MO).

EXAMPLE 2

Synthesis of cis-bis-cyclopentenecarboxylato1,2-DACH-platinum (II)

Cis-bis-cyclopentenecarboxylato-1,2-DACH-platinum (II) was one cis-platinum (CDDP) hydrophobic analog used as a prototype to develop liposomal-platinum (L-PT) preparations. The general structure of this particular complex was as follows:

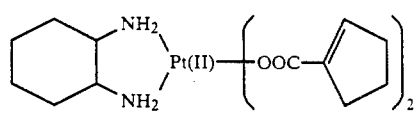

This prototype was synthesized using a multi-step procedure as described for racemic DACH (Khokhar et al. Inorg. Chem. Acta. Bioinorganic Section, V 108, p 63 (1985) follows: 0.96 g of DACH were added to a filtered aqueous solution of K₂PtCl₄ (3.5 g in 50 ml H₂O) and the mixture was stirred for six to eight hours at room temperature. The yellow solid containing cisbis-dichloro-DACH-Pt (II) was removed by filtration and washed with H$_2$O, methanol, and finally acetone. After the final product was dried under vacuum, the yield was calculated to be 56%. Subsequently, 1.0 g of cis-bis-dichloro-DACH-Pt (II) was suspended in 20 ml H$_2$O and an aqueous solution of Ag$_2$SO$_4$ (0.75 g in 150 ml H$_2$O) was added to obtain water soluble sulfato-DACH-Pt H$_2$O. The reaction mixture was stirred in the dark for 24 hours and the precipitated AgCl was removed by filtration. The yellow solution was evaporated to dryness at 45° C.–50° C. under reduced pressure and the yellow product was further dried over P$_2$O$_5$ in vacuum. The yield of sulfato-DACH-Pt (II) H$_2$O was 90%. Finally, 0.423 g (1 mmol) of sulfato-DACH-Pt (II) was dissolved in 100 ml of H$_2$O, and the barium cyclopentenecarboxylato was prepared in situ by the addition of 0.3 g of Ba(OH)$_2$ to 0.226 g (2 mmol) of cyclopentenecarboxylic acid in H$_2$O. These components were mixed and the reaction mixture was stirred for 30 minutes at room temperature. The BaSO$_4$ precipitate was filtered off, and the yellow filtrate was evaporated to dryness at 45° C. under reduced pressure using a rotary evaporator. A yellow solid was obtained, which was purified from methanol. The product was finally dried under vacuum. Yield was 70%. Analysis: C 40.26%, H 5.65% and N 5.05% C$_{18}$H$_{30}$H$_2$O$_4$Pt (PT) (theoretically C 40.67%, H 5.65% and N 5.27%. The infrared spectrum for the complex (as KBr pellet) /C=0 1632 cm$^{-1}$ and /C-0 1398 cm$^{-1}$.

Cis-bis-cyclopentenecarboxylato-1,2-DACH-Pt (II) is highly soluble in methanol and chloroform and only slightly soluble in water (less than 0.5 mg/ml). The above-described synthetic procedure was carried out with both trans-RR-DACH and trans SS-DACH to produce the trans-RR and trans-SS isomers of cis-bis-cyclopentenecarboxylato-1,2-DACH-Pt (II). The analysis of cis-bis-cyclopentenecarboxylato-1,2-trans-RR-DACH-Pt (II)-3H$_2$O was: C-37.36%, H-5.50%, N-5.12% (theoretically C-37.93%, H-5.82%, N-4.80%).

EXAMPLE 3

Synthesis of Cis-Bis-NeodecanoatoDACH-Platinum (II)

Sulfato-racemic-DACH-platinum (II) (0.423 g), prepared as described in Example 2, was dissolved in 10 ml water. A potassium salt of neodecanoic acid (0.420 g) was added to this solution and the reaction mixture stirred for 30 minutes at room temperature. A gummy mass was obtained which was extracted in chloroform and the chloroform extract was dried over anhydrous MgSO$_4$. The MgSO$_4$ was separated by filtration and the filtrate evaporated to dryness. An off-white solid product was obtained which was dried in vacuo and over P$_2$O$_5$. This final product was stored at 0° C.

The elemental analysis of the final product was: C-48.30%; H-8.10% and N-3.92%. The calculated elemental values for a compound of the empirical formula; C$_{26}$H$_{52}$N$_2$O$_4$Pt. is: C-47.93%; H-8.00% and N-4.30%.

The structural formula of the cis-bis-neodecanoatoDACH-platinum II was as follows:

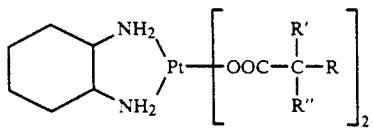

where R,R',R'' can be: CH$_3$, C$_2$H$_5$ or C$_3$H$_7$ to give a carboxylato radical function C$_{10}$H$_{19}$O$_2$ (MW = 172) as empirical formula.

Cis,bis-neodecanoato-DACH-platinum (II) was highly soluble in methanol and chloroform and insoluble in water.

The above described procedure was carried out with trans-RR-DACH to produce the trans-RR isomer of cis-bisneodecanoato-DACH-Platinum (II). The analysis of cis-bis-neodecanoato-RR-DACH-Platinum (II) was: C-47.75%, H-8.16%, N-3.98% (theoretically C-47.93%, H-8.00%, N-4.30%).

EXAMPLE 4

Synthesis of Cis-Bis-n-DecyliminodiacetatoDACH-Platinum (II)

Sulfato-DACH-platinum (II) H$_2$O (0.423 g), prepared as described in Example 2, was dissolved in 10 ml of H$_2$O. The sodium salt of n-decyliminodiacetic acid was prepared in situ by the addition of NaOH (0.08 g) to N-decyliminodiacetic acid (0.273 g) in 50 ml of water. This aqueous solution of sodium N-decyliminodiacetato was added to the sulfato-DACH-platinum solution and stirred for 30 minutes at room temperature. The resulting solution was evaporated to dryness on a rotary evaporator at 40° C. under reduced pressure. The yellow solid thus obtained was dissolved in methyl alcohol and filtered through Celite. The yellow filtrate was evaporated to dryness in a rotary evaporator under reduced pressure. A yellow crystalline product was obtained, which was further purified from 1-propanol, yield 80%.

An elemental analysis of the product showed: C-39.28; H-7.12% and N-6.68%. The theoretical composition for a compound of the empirical formula, C$_{20}$H$_{39}$N$_3$O$_4$Pt.2H$_2$O, was: C-38.95%; H-7.02% and N-6.81%. The infrared spectrum for the complex (as KBr.pellet)/ C=0 1580cm$^{-1}$ and / C-0 1410cm$^{-1}$.

The structural formula of the cis-bis-n-decyliminodiaceto-DACH-platinum (II) is shown as follows:

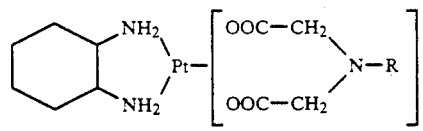

where R = n-decyl or a longer straight or branched chain alkyl radical.

Cis-bis-n-decyliminodiacetato-DACH-Platinum (II) is highly soluble in methanol and chloroform and insoluble in water. The above described synthetic procedure was carried out with trans-RR-DACH to produce the trans-RR isomer of cis-bis-n-decyliminodiacetato-DACH-Pt (II). The analysis of cis-bis-n-decyliminodiacetato-trans-RR-DACH-Pt (II) was: C-38.60%, H-6.87%, N-6.82% (theoretically C-38.95%, H-7.02%; N-6.81%).

The above described compound represents a structure where R$_1$ and R$_2$ of the earlier described general structure are one and the same and the carboxylato monoanions are bound together by a linking atom bearing an alkyl hydrophobic radical to form, in fact, a carboxylato dianion.

EXAMPLE 5

Platinum-Containing Liposomes (L-PT)

Multilamellar lipid vesicles (MLV) or liposomes containing incorporated platinum complexes (PT) of the above descriptions were prepared as previously described for other compounds (Lopez-Berestein et al (4)(1984) Clin. Exp. Metastasis V 2 pp 127-137 and Lopez-Berestein et al (1983) J Inf Dis V 147 pp 937-945). In brief, chloroform solutions of lipids (at the desired molar ratio) and PT were mixed at a lipid-PT ratio of 15:1 and the chloroform was evaporated in a rotary evaporator (Buchi, Brinkmann Instruments, Westbury, NY). The dried lipid film obtained, containing PT, was then dispersed with an aqueous solution (0.9% NaCl in water) by vigorous handshaking. The suspension was subsequently centrifuged at 30,000 ×g for 45 minutes, the supernatant was discarded, and the pellet containing PT was resuspended in 0.9% NaCl solution.

MLV or liposomes containing platinum complexes may also be prepared from a lyophilized powder containing lipid and platinum compound. The lipid and platinum compound are dissolved in the hydrophobic solvent tertiary butanol (M.P. 26° C.) at the ratios described above. The solution is freeze-dried and a white powder obtained. MLV containing the platinum compound are formed upon the addition of 0.9% NaCL solution in water to the yophilized powder with mild shaking by hand.

EXAMPLE 6

Calculation of Encapsulation Efficiency (EE) and Stability

Elemental platinum (Pt) was determined in the liposome suspension and the pellet by x-ray fluorescence as previously reported (Seifert et al (1979) Proc. Amer. Ass'n. Cancer Res. V 20 p. 168) in the Department of Analytical Chemistry, The University of Texas Medical School at Houston, TX. The amount of platinum complex (PT) was determined in the supernatant by ultraviolet (UV) spectrophotometry using a wavelength of 224 nm. The EE was initially calculated with the two following formulas:

1. EE = Pt in pellet/total Pt in the initial liposome suspension
2. EE = Total Pt initially added - Pt in supernatant-/total Pt initially added Since the results obtained by these two methods were highly comparable and the second method only requires PT determination by UV spectrophotometry, most EE determinations were calculated with the second method.

The stability of the different liposome-PT (L-PT) preparations in 0.9% NaCl solution at 4° C., and 50% human (AB) serum in 0.9% NaCl solution at 37° C. was determined using the following formula:

$$\text{Stability at } x \text{ hours} = \frac{\% EE \text{ at } x \text{ hours}}{\% EE \text{ at } 0 \text{ hours}} \times 100$$

The EE values used in the stability determinations were obtained by measuring PT in the supernatants by UV spectrophotometry (0.9% NaCl solution) or x-ray fluorescence (50% human AB serum). The stability in 0.9% NaCl solution was determined up to 14 days after the initial preparation. In addition, the L-PT preparations were observed microscopically on day 14 to check the morphology of the vesicles. The stability in 50% human AB serum was determined up to 18 hours after incubation.

Different cis-platinum analogs were encapsulated in multilamellar vesicles composed of DMPC:DMPG 7:3. The encapsulation efficiency for Pt-cyclopentenecarboxylato racemic-DACH was 66%. The encapsulation efficiency was significantly increased when the pure trans RR DACH or trans-SS-DACH isomers were used (88% and 90%, respectively). The encapsulation efficiency for Pt-neodecanoato-racemic-DACH, Pt-neodecanoato trans-RR-DACH, Pt-n-decyliminodiacetato racemic DACH complexes are presented in Table I, shown below.

TABLE 1
ENCAPSULATION EFFICIENCY OF L-PT USING DIFFERENT ANALOGUES

| Platinum Analogue | % Encapsulation Efficiency[1] |
|---|---|
| Pt-cyclopentenecarboxylato racemic-DACH mixture | 66 |
| Pt-cyclopentenecarboxylato trans-RR-DACH | 88 |
| Pt-cyclopentenecarboxylato trans-SS-DACH | 90 |
| Pt-neodecanoato-racemic DACH-mixture | 99 |
| Pt-neodecanoato-trans-RR-DACH | 99 |
| Pt-N-decyliminodiaceto-racemic-DACH mixture | 100 |
| Pt-N-decyliminodiacetato-trans-RR-DACH | 98 |

[1]Mean of at least three experiments. Liposome composition: DMPC:DMPG 7:3

Analogous experiments (not shown) with DMPC alone, DMPG alone, cholesterol alone, DMPC and DPMG combined in other concentrations, with or without cholesterol showed no better encapsulation efficiency and, most frequently, a significantly decreased EE.

EXAMPLE 7

Stability of L-PT in Aqueous Milieu

Preparations were suspended in 0.9% saline and incubated at 4° C. for 14 days. The liposome compositions were observed by light microscopy and the amount of free PT in the saline determined. Liposomes containing PT and composed of DMPG as the only phospholipid showed significant microscopically determined loss of structure. Free PT was determined and stability was calculated as the percentage PT remaining in the liposomes. The results of these measurements are presented in Table 2 below.

TABLE 2
STABILITY OF L-PT IN SALINE L-PT AT 14 DAYS[1]

| Platinum Analog | Stability % |
|---|---|
| Pt-cyclopentenecarboxylato-racemic-DACH | 89 |
| Pt-cyclopentenecarboxylato-trans-RR-DACH | 94 |
| Pt-cyclopentenecarboxylato-trans-SS-DACH | — |
| Pt-neodecanoato-racemic-DACH | 100 |
| Pt-neodecanoato-trans-RR-DACH | 99 |
| Pt-iminodiacetato-racemic-DACH | 100 |
| Pt-iminodiacetato-trans-RR-DACH | 100 |

[1]Liposome composition: DMPC:DMPG 7:3

As may be seen in the above data, both the Pt cyclopentenecarboxylato trans-RR-DACH and the Pt-neodecanoato-racemic-DACH exhibit greater stability than the Pt cyclopentenecarboxylato-racemic-DACH.

EXAMPLE 8

Toxicity Studies of L-PT
(Cyclopentenecarboxylato-racemic-DACH)

Toxicology studies were carried out in 6-8 weeks old CD-1 Swiss mice weighing 22-25 gm and purchased from The University of Texas Science Park (Bastrop, TX). Free PT in suspension in hydroxypropylcellulose, DMPG, DMPG-PT, DMPC:DMPG 7:3 and DMPC:DMPG 7:3-PT were administered intraperitoneally (ip) in volumes ranging between 0.1 and 0.3 ml. DMPC:DMPG 7:3-PT was also administered intravenously (iv) in one single injection or in 3 daily injections. The clinical behavior and the survival times were monitored on a daily basis. The $LD_{10}$, $LD_{50}$ and $LD_{90}$ were calculated considering the deaths occurring up to 14 days after injection.

PT in suspension in hydroxypropylcellulose, DMPG-PT and DMPC:DMPG 7:3-PT had a similar $LD_{50}$ dose level when given in a single intraperitoneal (ip) injection (91 mg/kg, 86 mg/kg and 75 mg/kg respectively) (Table 3). The amount of PT that would be encapsulated at the $LD_{50}$ dose level of empty liposomes composed of DMPG and DMPC:DMPG 7:3 was higher (183 mg/kg and >304 mg/kg respectively). The $LD_{50}$ dose for DMPC:DMPG 7:3-PT injected iv was similar for the two schedules used: single injection and daily ×3 injections (82 mg/kg vs 96 mg/kg). Most deaths in both the ip and iv toxicity studies occurred between day 5 and 10 after injection. The results of these studies are presented in Table 3.

TABLE 3

TOXICITY OF DIFFERENT L-PT PREPARATIONS
(CYCLOPENTENECARBOXYLATO-RACEMIC-DACH)
ADMINISTERED IP AND IV

| L-PT Preparation | Route of Administration | $LD_{10}$ mg/kg | $LD_{50}$ mg/kg | $LD_{90}$ mg/kg |
|---|---|---|---|---|
| Free PT | ip × 1 | 61 | 91 | 125 |
| DMPG-PT | ip × 1 | 56 | 86 | 133 |
| DMPC:DPMG 7:3-PT | ip × 1 | 54 | 75 | 94 |
|  | iv × 1 | — | 82 | 100 |
|  | iv qd × 3 | 63 | 86 | 107 |
| DMPG* | ip × 1 | 158 | 183 | 228 |
| DMPC:DMPG 7:3* | ip × 1 | >304 | >304 | >304 |

*Results expressed in mg/kg of PT that would be encapsulated at the $LD_{10}$, $LD_{50}$ and $LD_{90}$ dose levels of empty liposomes.

EXAMPLE 9

NEPHROTOXICITY

Blood urea nitrogen (BUN) was determined in samples obtained from the retroorbital plexus of $CD_1$ Swiss mice weighing 22-25 gm 96 hours after the ip injection (single dose) of CDDP, PT cyclopentenecarboxylato racemic DACH in hydroxypropylcellulose, DMPG-PT or DMPC:DMPG 7:3-PT at doses corresponding to the previously determined $LD_{50}$. All L-PT preparations tested for toxicity were prepared under sterile conditions on the same day of the experiments. There were no significant BUN elevations after the ip administration of the $LD_{50}$ dose of PT in suspension in hydroxypropylcellulose, DMPG-PT and DMPC:DMPG 7:3-PT (BUN at 96 hours 34.4±9.6 mg %, 30.0±4.6 mg % and 32.0±2.3 mg % respectively). The results are shown below in Table 4.

TABLE 4

ACUTE NEPHROTOXICITY OF CDDP, FREE PT
(CYCLOPENTENECARBOXYLATO-RACEMIC-DACH)
AND L-PT AT THE $LD_{50}$ DOSE IN $CD_1$ MICE

| Preparation | $LD_{50}$ Dose ip Single Injection (mg/kg) | BUN at 96 hours[1] (mg %) |
|---|---|---|
| CDDP | 17 | 78.3 ± 8.0 |
| Free PT | 91 | 34.4 ± 9.6 |
| DMPG-PT | 86 | 30.0 ± 4.6 |
| DMPC:DMPG 7:3 | 75 | 32.0 ± 2.3 |

[1]Normal = 27.2 ± mg %

EXAMPLE 10

In Vitro Antitumor Activity of Cyclopentenecarboxylato-RacemicDACH-Pt Against L1210 Cells L1210 leukemic cells were grown in a suspension culture in McCoy's 5A medium (Gibco Laboratories, Grand Island, NY) supplemented with 10% horse serum, glutamine, streptomycin and penicillin at 37° C., 95% relative humidity in a 5% $CO_2$ atmosphere. Four ml of cell suspension were added to culture tubes and the appropriate concentration of free PT or L-PT was added (from 0.01 micro g/ml to 10 micro g/ml final concentration). After 96 hours, the cell concentration of control and experimental cultures were calculated with a Coulter Counter (Coulter Electronics, Hialeah, FLA) and the percent inhibition calculated. The following preparations were tested: free PT, DMPG, DMPC:DMPG 7:3, DMPG-PT and DMPC:DMPG 7:3-PT. Results were expressed as the dose achieving a 50% growth inhibition ($ID_{50}$) Results for empty liposomes were expressed as the amount of PT that would have been encapsulated at the $ID_{50}$ concentration.

The $ID_{50}$ for free cyclopentenecarboxylato-racemic DACH was 1.3 micro g/ml (Table 5). Of the two L-PT preparations tested, DMPG-PT was slightly more active than DMPC:DMPG 7:3-PT (mean $ID_{50}$ of three experiments; 0.7 and 1.6 micro g/ml respectively). Empty liposomes composed of DMPG had an $ID_{50}$ of 3.7 micro g/ml while the $ID_{50}$ for empty liposomes composed of DMPC:DMPG 7:3 was >10 micro g/ml (Table 5).

TABLE 5

IN VITRO ANTITUMOR ACTIVITY AGAINST L1210
CELLS OF FREE PT, L-PT AND EMPTY LIPOSOMES
(where PT is cyclopentenecarboxylato-racemic-DACH-PT)

| Preparation | $ID_{50}$ (micro g/ml)[1] | | | |
|---|---|---|---|---|
|  | Exp. 1 | Exp. 2 | Exp. 3 | Mean |
| Free PT | 1.3 | — | — | — |
| DMPG-PT | 0.7 | 1.0 | 1.4 | 0.7 |
| DMPG[2] | 3.0 | 3.0 | 5.0 | 3.7 |
| DMPC:DMPG 7:3-PT | 1.9 | 2.0 | 0.9 | 1.6 |
| DMPC:DMPG 7:3[2] | >10.0 | — | — | — |

[1]CDDP $ID_{50}$ = 0.1 micro g/ml
[2]$ID_{50}$ expressed as micro g/ml of PT that would be encapsulated at the $ID_{50}$ concentration of empty liposomes.

EXAMPLE 11

In Vivo Antitumor Activity of L-PT Against L1210 Mouse Leukemia where PT is cyclopentenecarboxylato-racemic-DACH The in vivo antitumor activity of CDDP, PT in hydroxypropylcellulose, DMPG, DMPG-PT, DMPC:DMPG 7:3, and DMPC:DMPG 7:3-PT was tested in an L1210-BDF$_1$ mouse model (25). BDF$_1$ mice were purchased from Charles River (Wilmington, MA). Groups of 6-8 mice weighing 18-22 gm were inoculated ip with $1 \times 10^6$ L1210 leukemia cells on day 0. L1210 cells were kept in DBA$_2$ mice were weekly passages between the different experiments. All L-PT preparations were injected ip in volumes of 0.1 to 0.3 ml 24 hours after tumor inoculation. Two different schedules of administration were used: a single injection on day 1 or an injection on days 1, 5 and 9 (multiple). The doses of CDDP used were the ones that had resulted in a maximum antitumor activity in previous experiments. The doses of PT, DMPG-PT and DMPC:DMPG 7:3-PT used ranged from 3.125 mg/kg to 50 mg/kg (approximate LD$_{10}$). Clinical behavior and survival times were monitored until all animals had died. Results were expressed as % T/C (median survival time of treated mice/median survival time of control mice $\times 100$) and number of long-term survivors. Mice living more than 30 days and more than 60 days were considered to be long-term survivors for the single and multiple injection schedule respectively. All L-PT preparations tested for antitumor activity were prepared under sterile conditions on the same day of the experiment. In the first set of experiments, the effect of a single ip dose of CDDP, free PT, DMPG-PT and DMPC:DMPG 7:3-PT in the treatment of L1210 leukemia was tested. Mice treated with free PT at doses of 12.5 mg/kg and 25 mg/kg had a % T/C comparable to those treated with 10 mg/kg of CDDP (162 vs 178, means of three experiments) (Table 6). DMPG-PT at doses of 12.5 mg/kg, 6.25 mg/kg and 3.125 mg/kg had an antitumor activity comparable to free PT and CDDP (mean % T/C=175 for 12.5 mg/kg; 158 for 6.25 mg/kg; and 163 for 3.125 mg/kg) (Table 6). Doses of DMPG-PT of 25 mg/kg or more were toxic for L1210 leukemia-bearing BDF$_1$ mice. Mice treated with DMPC:DMPG 7:3-PT at doses of 25 mg/kg, 12.5 mg/kg and 6.25 mg/kg had a similar or slightly higher % T/C than those obtained with CDDP, free PT and DMPG-PT (mean: % T/C=215 for 25 mg/kg; 178 for 12.5 mg/kg; and 200 for 6.25 mg/kg) (Table 6). DMPC:DMPG 7:3-PT at a dose of 50 mg/kg was toxic for L1210 leukemia-bearing BDF$_1$ mice. Empty liposomes composed of DMPG and DMPC:DMPG 7:3, at doses equivalent to the optimal ones of loaded vesicles (L-PT) did not shown antitumor activity (% T/C=105 for DMPG and 93 for DMPC:DMPG 7:3). Long-term survivors (one or two mice of six) were seen in the groups treated with CDDP, DMPG-PT and DMPC:DMPG 7:3-PT (Table 6).

In the experiment using a multiple dose schedule, the highest % T/C obtained was 253 for CDDP 7.5 mg/kg $\times 3$, 284 for free PT 12.5 mg/kg $\times 3$, 179 for DMPG-PT 6.25 mg/kg $\times 3$ and 403 for DMPC:DMPG 7:3-PT 12.5 mg/kg $\times 3$. Long-term survivors (1 of 6 mice) were only observed in the group treated with DMPC:DMPG 7:3-PT (Table 7).

TABLE 6

IN VIVO ANTITUMOR ACTIVITY AGAINST MOUSE L1210 LEUKEMIA OF CDDP, FREE PT AND L-PT ADMINISTERED IP (DAY 1) where PT is cyclopentenecarboxylato-racemic-DACH

| Group Number | Preparation[4] | | % T/C (Number of Survivors on Day 30) | | |
|---|---|---|---|---|---|
| | | | Exp. 1[1] | Exp. 2[2] | Exp. 3[3] |
| 1 | CDDP | 10 mg/kg | 167 | — | 189 (1/6) |
| 2 | Free PT | 25 mg/kg | — | — | 168 |
| 3 | | 12.5 mg/kg | 173 | 136 | 179 |
| 4 | DMPG-PT | 25 mg/kg | 100 | — | — |
| 5 | | 12.5 mg/kg | 160 | 209 (2/6) | 158 |
| 6 | | 6.25 mg/kg | — | — | 158 |
| 7 | | 3.12 mg/kg | — | — | 163 (2/6) |
| 8 | DMPC:DMPG 7:3-PT | 25 mg/kg | 213 | 200 (1/6) | 232 (1/6) |
| 9 | | 12.5 mg/kg | 167 (1/6) | — | 189 (1/6) |
| 10 | | 6.25 mg/kg | — | — | 200 |

[1]median survival of control = 7.5 days
[2]median survival of control = 11 days
[3]median survival of control = 9 days
[4]All preparations were injected ip in 0.1-0.3 ml 24 hours after the ip inoculation of $1 \times 10^6$ L1210 cells.

TABLE 7

IN VIVO ANTITUMOR ACTIVITY AGAINST MOUSE L1210 LEUKEMIA OF CDDP, FREE PT AND L-PT ADMINISTERED IP (DAYS 1, 5 and 9) WHERE PT IS CYCLOPENTENECARBOXYLATO-RACEMIC-DACH

| Group Number | Preparation[1] | Dose | % T/C (Number of Survivors on Day 60) |
|---|---|---|---|
| 1 | CDDP | 7.5 mg/kg × 3 | 253 |
| 2 | Free PT | 25 mg/kg × 3 | 158 |
| 3 | | 12.5 mg/kg × 3 | 284 |
| 4 | | 6.25 mg/kg × 3 | 168 |
| 5 | DMPG-PT | 12.5 mg/kg × 3 | 105 |
| 6 | | 6.25 mg/kg × 3 | 179 |
| 7 | | 3.12 mg/kg × 3 | 168 |
| 8 | | 1.56 mg/kg × 3 | 115 |
| 9 | DMPC:DMPG 7:3-PT | 12.5 mg/kg × 3 | 403 (1/6) |
| 10 | | 6.25 mg/kg × 3 | 253 |
| 11 | | 3.125 mg/kg × 3 | 210 (1/6) |

[1]All preparations were injected ip in volumes of 0.1 to 0.3 ml 24 hours, 5 days and 9 days after tumor inoculation

EXAMPLE 12

In Vivo Antitumor Activity of Different L-PT Analogs Against L-1210 Leukemia

The antitumor activity against L-1210 murine leukemia of the different L-PT analogs was assessed in an L-1210-BDF$_1$ mouse model (tumor inoculation day 0, treatment day 1, ip) as described earlier herein. Compared with CDDP (% T/C=175), the L-PT analogs showed equivalent or slightly higher anti-tumor activity, with the exceptions of L-PT (cyclopentenecarboxylato trans-SS-DACH =155 and N-decyliminodiaceto racemic-DACH =150 and N-decyliminodiaceto trans-RR-DACH =162). These results are shown in Table 8.

TABLE 8

ANTITUMOR EFFECT AGAINST L1210 LEUKEMIA[3] OF CIS-PLATINUM AND DIFFERENT LIPOSOMAL-PLATINUM ANALOGUES[1]

| Platinum Analog | Dose[4] mg/kg | % T/C[2] |
|---|---|---|
| PT-cyclopentenecarboxylato-racemic-DACH | 25 | 213 |
| PT-cyclopentenecarboxylato-trans-RR-DACH | 25 | 187 |
| PT-cyclopentenecarboxylato-trans-SS-DACH | 25 | 155 |
| PT-neodecanoato-racemic-DACH | 50 | 187 |
| PT-neodecanoato-trans-RR-DACH | 25 | 175 |
| PT-N-decyliminodiacetato-racemic-DACH | 25 | 150 |
| PT-N-decyliminodiacetato trans-RR-DACH | 25 | 162 |
| Cis-platinum (CDDP)[5] | 10 | 175 |

[1] Liposome composition: DMPC:DMPG 7:3
[2] Median survival of treated mice/Median survival of control mice × 100
[3] 1 × 10[6] L1210 cells inoculated ip on day 0.
[4] Treatment: ip on day 1
[5] Dissolved in saline. 1 mg/ml

EXAMPLE 13

In Vivo Antitumor Activity of L-PT-NEODECANOATO-RACEMIC-DACH Against Liver Metastases of Mouse M5076 Reticulosarcoma The potential antitumor effect of L-PT against liver metastases was tested using L-PT-NEODECANOATO-RACEMIC-DACH prepared as described in Example 6 and the mouse M5076 reticulosarcoma, which is a tumor that metastasizes exclusively to the liver.

L-PT-NEODECANOATO-RACEMIC-DACH was more active than cis-platinum in the treatment of established liver metastases of M5076 using two different tumor inocula and schedules of administration (Table 9 and 10). L-PT-NEODECANOATO-RACEMIC-DACH (25 mg/kg on days, 8, 12, 16) resulted in a more than two fold reduction in the number of liver metastases compared with cis-platinum (7.5 mg/kg on days, 8, 12, 16) on day 30 after the intravenous inoculation of 10[5] M5076 cells (mean number of liver metastases ±SD =39 ±21 for L-PT vs 114 ±38 for cisplatinum (Table 9). L-PT-NEODECANOATO-RACEMIC-DACH (25 mg/kg on days 4, 8, 12) resulted in the complete inhibition of liver metastases of M5076 on day 45 after the inoculation of 10[4] M5076 cells, while 4/6 animals treated with cis-platinum (7.5 mg/kg on days 4, 8, 12) had 175 or more liver metastases (Table 10).

L-PT-NEODECANOATO-RACEMIC-DACH was effective in the prophylaxis of liver metastases of M5076 reticulosarcoma. L-PT-NEODECANOATO-RACEMIC-DACH (37.5 mg/kg on day −1) resulted in a five-fold decrease in the number of liver metastases on day 21 after the intravenous inoculation of 10[4] M5076 cells (inoculation day 0) compared with cis-platinum (10 mg/kg on day −1) and untreated animals (mean number of liver metastases ±SD =52 ±20 for L-PT, 256 ±54 for cis-platinum, and 226 ±21 for control) (Table 11).

TABLE 9

Treatment of Liver Metastases of M5076 Reticulosarcoma with L-PT-NEODECANOATO-RACEMIC-DACH

| Day 30 Treatment | Dose mg/kg | Schedule day | No. Liver Metastases on mean ± SD |
|---|---|---|---|
| Cis-platinum | 7.5 | 8, 12, 16 | 114 ± 38 |
| L-PT-NEODECANOATO-RACEMIC-DACH | 25 | 8, 12, 16 | 39 ± 21 |

*Groups of 10 C57BL/6 mice were inoculated on day 0 with 10[5] M5076 cells intravenously. Animals were treated on days 8, 12, and 16 with cis-platinum or L-PT-NEODECANOATO-RACEMIC-DACH. The median survival of untreated animals was 19 days. Treated animals were sacrificed on day 30, the livers dissected, placed in Bouin's fixative, and the number of liver-tumor colonies counted.

TABLE 10

Treatment of Liver Metastases of M5076 Reticulosarcoma with L-PT-NEODECANOATO-RACEMIC-DACH

| Day 45 Treatment | Dose mg/kg | Schedule day | No. Liver Metastases on mean ± SD |
|---|---|---|---|
| Cis-platinum | 7.5 | 24, 8, 12 | 0, 0, 175, >200, >200, >200 |
| L-PT-NEODECANOATO-RACEMIC-DACH | 25 | 4, 8, 12 | 0, 0, 0, 0, 0, 1 |

*Groups of 6 C57BL/6 mice were inoculated on day 0 with 10[4] M5076 cells intravenously. Animals were treated on days 4, 8, and 12 with cis-platinum or L-PT-NEODECANOATO-RACEMIC-DACH. The median survival of untreated animals was 30 days. Treated animals were sacrificed on day 45, the livers dissected, placed in Bouin's fixative, and the number of liver-tumor colonies counted. Two of the animals treated with cis-platinum died before day 45 versus none in the group treated with L-P.

TABLE 11

Prophylaxis of Liver Metastases of M5076 Reticulosarcoma with L-PT-NEODECANOATO-RACEMIC-DACH*

| Day 21 Treatment | Dose mg/kg | Schedule day | No. Liver Metastases on mean ± SD |
|---|---|---|---|
| None | — | — | 226 ± 21 |
| Cis-platinum | 10 | −1 | 256 ± 54 |
| L-PT-NEODECANOATO-RACEMIC-DACH | 37.5 | −1 | 52 ± 20 |

*Groups of 6 C57BL/6 mice were treated on day −1 with cis-platinum or L-PT Neodecanoato-Racemic-DACH. Animals were inoculated on day 0 with 10[4] M5076 cells intravenously. The median survival of untreated animals was 21 days. Treated animals were sacrificed on day 21, the livers dissected, placed in Bouin's fixative, and the number of tumor colonies counted.

EXAMPLE 14

Preparation of cis-bis-neodecanoatocis-diamine-platinum (II).

Cis-diamine-diiodo-platinum (II) $(NH_3)_2$ $Pt-I_2$ was first prepared by the following method:

$K_2PtCl_4$ (5 g) was dissolved in water (20 ml). An aqueous solution of KI (3 g) was added and a dark brown solution was obtained. Aqueous concentrated ammonia (2 ml) was added to the mixture which was stirred for 2-3 hr. at room temperature. The mixture was filtered and the solid was washed with an excess of water, ethanol and ether. The product was dried over $P_2O_5$ under vacuum. Yield 4.5 g (77%).

The compound according to the invention was then prepared as follows:

$(NH_3)_2$-$Pt-I_2$ (1.0 g) was suspended in water (50 ml), and aqueous solutions of $AgNO_3$ (0.68 g 20 ml $H_2O$) was added thereto. The reaction mixture was stirred overnight at room temperature in the dark. The AgI precipitate was filtered and filtrate was concentrated by rotary evaporation. To the concentrated solution a solution of sodium neodecanoato prepared in situ, (neodecanoic acid 0.688 g in 20 ml methanol and 1N NaOH, 4 ml) was added. The reaction mixture was stirred overnight at room temperature. The yellow reaction mixture was evaporated to dryness at 40° C. under reduced pressure using a rotary evaporator. A gummy product was obtained which was extracted in chloroform and the chloroform extract was dried over anhydrous MgSO$_4$. MgSO$_4$ was separated by filtration and filtrate was evaporated to dryness under reduced pressure using a rotary evaporator. A cream-color solid was obtained which was dried over P$_2$O$_5$ in vacuo. The final product was stored at 0° C.

The elemental analysis of the final product was C41.58, H8.03; N 4.45%. The calculated values for C$_{20}$H$_{44}$N$_2$4Pt. is C42.00; H7.7, N4.90%.

The structural formula of the cis-bis-neodecanoato-bis-diamine-platinum (II), is as follows:

where R, R', R" can be CH$_3$, C$_2$H$_5$ or C$_3$H$_7$ to give a carboxylato radical function with C$_{10}$H$_{19}$O$_2$ (MW =171) as empirical formula.

Cis-bis-neodecanoato-bis-diamine-platinum (II) is highly soluble in chloroform, methanol and other common organic solvents, but insoluble in water.

EXAMPLE 15

Preparation of cis-bis-neodecanoato-bis cyclohexylamine-platinum (II) dihydrate

The method of Example 14 was followed, using the cyclohexylamine ligand in place of ammonia. The complex is highly soluble in chloroform, methanol and other organic solvents, but insoluble in water.

Elemental Analysis; Calculated for C$_{32}$H$_{64}$N$_2$O$_4$.2·H$_2$O, C49.71; H8.80, N3.62%, found C49.31; H8.39; N3.16%

The structural formula of the cis-bis-neodecanoato-bis-cyclohexylamine-platinum (II) is as follows:

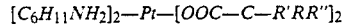

where R, R', R" can be CH$_3$, C$_2$H$_5$ or C$_3$H$_7$ to give a carboxylato radical functions C$_{10}$H$_{19}$O$_2$ (MW =171) as empirical formula.

EXAMPLE 16

Preparation of cis-bis-neodecanoatoethylenediamine-platinum (II) H$_2$O.

Cis-diiodo-ethylenediamine-platinum (II), was first prepared by the method of Example I, using ethylenediamine ligand in place of ammonia and with a 96% yield of product.

Sulfate-ethylenediamine-platinum (II). H$_2$O was prepared by the following method.

Cis-bis-diiodo-ethylenediamine-platinum (II), (3.9) was suspended in 10 ml H$_2$O and an aqueous solutions of Ag$_2$SO$_4$ (2.2 g in 200 ml H$_2$O) was added thereto. The reaction mixture was stirred in the dark overnight at room temperature. AgI was removed by filtration and the yellow filtrate was evaporated to dryness at 40° C.–45° C. under reduced pressure using rotary evaporation. The final product was dried over P$_2$O$_5$ under vacuum. The product yield was 2.35 g (81%).

The compound according to the invention was then prepared as follows:

Sulfate-ethylenediamine-platinum (II), H$_2$O (0.369 g) was dissolved in H$_2$O (20 ml) and a solution of sodium neodecanoato prepared in situ (neodecanoic acid, 0.344 g in 20 ml methanol and 1N NaOH, 2 ml) was added thereto. The reaction mixture was stirred for 2–3 hr. at room temperature. The reaction mixture was evaporated to dryness at 40° C.–45° C. under reduced pressure using rotary evaporation. A gummy product was obtained which was extracted in chloroform and the chloroform extract was dried over anhydrous MgSO$_4$. The MgSO$_4$ was separated by filtration and the filtrate was evaporated to dryness under reduced pressure using a rotary evaporator. The final product was dried over P$_2$O$_5$ in vacuo. The product was stored at 0° C.

Elemental analysis; calculated for C$_{22}$H$_{46}$N$_2$O$_4$Pt. H$_2$O, C42.86; H7.79; N 4.54%, found C43.07; H 7.32; N 4.71%.

Cis-bis-neodecanoato-ethylenediamine-platinum (II) is highly soluble in chloroform, methanol and other organic solvents, but insoluble in water.

The structural formula of the cis-bis-neodecanoato-ethylenediamine-platinum (II) is as follows:

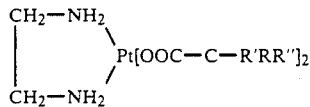

where R, R', R" can be CH$_3$, C$_2$H$_5$ or C$_3$H$_7$ to give a carboxylato radical function C$_{10}$H$_{19}$O$_2$ (MW =171) as empirical formula.

EXAMPLE 17

Preparation of cis-bis-neodecanoatobis-isopropylamine-platinum (II)

Cis-bis-neodecanoato-bis-isopropylamine-platinum (II) and sulfato-bis-isopropylamineplatinum (II) were first prepared by the method of Example 16, using isopropylamine ligand in place of ethylenediamine.

The compound according to the invention was then prepared as follows:

Sulfato-bis-isopropylamine-platinum (II). H$_2$O (0.427 g) was dissolved in H$_2$O (50 ml) and a solution of sodium-neodecanoato prepared in situ (neodecanoic acid 0.344 g in 20 ml of methanol and 1N NaOH, 2 ml) was added thereto. The reaction mixture was stirred for 2–3 hr. at room temperature. The reaction mixture was evaporated to dryness at 0° C.–45° C. under reduced pressure using rotary evaporator. A gummy mass was obtained which was extracted in chloroform and the chloroform extract was dried over anhydrous MgSO$_4$. The MgSO$_4$ was separated by filtration and filtrate was evaporated to dryness under reduced pressure using a rotary evaporator. The product was dried over P$_2$O$_5$ in vacuo. The final product was stored at 0° C.

Elemental analysis, calculated for C$_{26}$H$_{56}$N$_2$O$_4$Pt, C47.63; H8.53; N4.26%; found C 47.74; H8.47; N 3.93%.

The structural formula of the cis-bis-neodecanoato-bis-isopropylamine-platinum (II) is as follows:

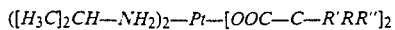

where R, R', R" can be CH$_3$, C$_2$H$_5$ or C$_3$H$_7$ to give a carboxylato radical function with C$_{10}$H$_{19}$O$_2$ (MW =171) as an empirical formula.

Cis-bis-neodecanoato-bis-isopropylamine-platinum (II), is highly soluble in chloroform, methanol and other organic solvents, but insoluble in water.

EXAMPLE 18

Preparation of cis-bis-decanoato-transR,R-1,2-diaminocyclohexane-platinum II.

Sulfato-trans-R,R-1,2-diaminocyclohexane-platinum II $H_2O$ (0.423 g) was dissolved in $H_2O$ (20 ml) and a solution of sodium-decanoato prepared in situ (0.344 g decanoic acid in 20 ml methanol and 1N NaOH 2 ml) was added thereto. The reaction mixture was stirred for 2-3 hr. at room temperature. The reaction mixture was evaporated to dryness at 40° C.-45° C. under reduced pressure using a rotary evaporator. A solid was obtained which was extracted in chloroform and chloroform extract was dried over anhydrous $MgSO_4$. The $MgSO_4$ was removed by filtration and filtrate was evaporated to dryness under reduced pressure using rotary evaporator. The product was dried over $P_2O_5$ in vacuo. The final product was stored at 0° C.

Elemental analysis - calculated for $C_{26}H_{52}N_2O_4Pt\cdot H_2O$ C46.59; H8.06; N 4.18%, found C 45.94; H7.87 N 4.31%.

Cis-bis-decanoato-trans-R,R-1,2-diaminocyclohexaneplatinum II is highly soluble in chloroform and other organic solvents, but insoluble in water.

The structural formula of the cis-bis-decanoato-trans-R,R-1,2-diaminocyclohexane-platinum II is as follows:

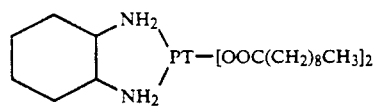

EXAMPLE 19

Cis-bis-neopentanoato-trans-R,R-1,2-diaminocyclohexane-platinum II.

Sulfato-trans-R,R-1,2-diaminocyclohexane-platinum II. $H_2O$ (0.423 g) was dissolved in water (20 ml) and a solution of barium-neopentanoato prepared in situ (neopentanoic acid, 0.204 g, in 5 ml of methanol and Ba(OH)$_2\cdot$8H$_2$O 0.3 g in 50 ml $H_2O$ combined together) was added thereto. The reaction mixture was stirred for 2-3 hr. at room temperature. The reaction mixture was evaporated to dryness at 40° C.-45° C. under reduced pressure using a rotary evaporator. The residue was extracted with methanol, filtered and the filtrate was evaporated to dryness. A solid was obtained which was further extracted with chloroform. The chloroform extract was evaporated to dryness and a cream-color product was obtained. The product was dried over $P_2O_5$ under vacuum.

Elemental analysis calculated for $C_{16}H_{32}N_2O_4Pt\cdot2H_2O$; C35.00; H6.57; N5.11%, found C35.16; H6.17; N5.27%.

Cis-bis-Neopentanoato-trans-R,R-1,2-diaminocyclohexane-platinum II, is highly soluble in chloroform, methanol and other common organic solvents.

The structural formula of the cis-bis-neopentanoato-trans-R,R-1,2-diaminocyclohexane-platinum II is as follows:

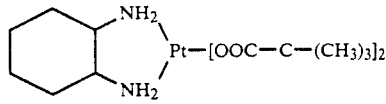

EXAMPLE 20

Encapsulation efficiency and antitumor activity of lipophilic cisplatin analogs

The compounds prepared in Examples 14-19 were tested for their efficiency of encapulation in liposomes by the methods described in Example 6. These liposome-encapsulated compounds were tested to determine their optimal dose and effectiveness as inhibitors of in vivo tumor growth as described in Example 12. The data in Table 12 reveal the resultant measurements.

TABLE 12

Encapsulation Efficiency and Antitumor Activity of Lipophilic Cisplatin Analogues Incorporated in Liposomes

| Compound | Encapsulation Efficiency | Optimal dose mg/kg | % T/C L1210 ip/ip single dose |
|---|---|---|---|
| Cis-bis-neodecanoato-cis-diamine-platinum (II) | 95% | 50 | 200 |
| Cis-bis-neodecanoato-bis-cyclohexylamine-platinum (II) | 89% | 100 | 125 |
| Cis-bis-neodecanoato-ethylenediamine-platinum (II) | 82% | 75 | 144 |
| Cis-bis-neodecanoato-bis-isopropylamine-platinum (II) | 87% | 100 | 150 |
| Cis-bis-decanoato-trans-R,R-1,2-diaminocyclohexane-platinum (II) | 96% | 50 | 187 |
| Cis-bis-neodecanoato-trans-R,R-1,2-diaminocyclohexane-platinum (II) | 93% | 25 | 170 |

EXAMPLE 21

In Vitro cytotoxicity against human malignant cell lines

Cis-bis-neodecanoato-1,2-diaminocyclohexane platinum (II) was tested in the liposomal-form against three human malignant cell lines of colon carcinoma (LoVo, SW620, and SW403) using a colony formation inhibition assay. The drug concentration that resulted in a 50% inhibition of colony formation (IC50) ranged from 4 to 8 $\mu$M. The IC50 of cisplatinum for these same cell lines ranged from 3 to 7 $\mu$M.

Changes may be made in the various compositions, elements, steps and procedures described herein without departure from the concept and scope of the invention as defined in the following claims.

What is claimed is:

1. A platinum (II) four-coordinate complex having the formula:

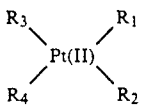

wherein $R_1$ and $R_2$ are each alkyl carobylato bearing a hydrophobic radical function or, when linked together, are a dicarboxyl to bearing a hydrophobic radical function, and wherein $R_3$ and $R_4$ are each amines of the formula: wherein $R_5$ is selected from the group consisting of hydrogen, alky, aryl, aralkyl, alkenyl, cycloalkyl, or cycloalkenyl having between 1 and 20 carbon atoms; or wherein $R_3$ and $R_4$, when linked together, are selected from the group consisting of cycloalkyl-1,2-diamino having between about 3 and 7 carbon atoms, and alkyl-vicinal-diamino having between about 3 and 12 carbon atoms; and said complex is defined further as being substantially soluble in methanol or chloroform and substantially insoluble in water.

2. The complex of claim 1 wherein $R_5$ has between 6 and 12 carbon atoms.

3. The complex of claim 1 wherein $R_5$ has between about 2 and 6 carbon atoms.

4. The complex of claim 1 wherein the dicarboxylato has between about 5 and 20 atoms.

5. The complex of claim 1 wherein $R_5$ is an alkenyl having between about 5 and 20 carbon atoms.

6. The complex of claim 1 wherein $R_5$ is an cycloalkyl having between about 3 and 12 carbon atoms.

7. The complex of claim 1 wherein the aralkyl is defined further as containing linked aryl and alkyl portions and having between 7 and 20 carbon atoms.

8. The complex of claim 7 wherein the aryl portion has between 6 and 10 carbon atoms.

9. The complex of claim 7 wherein the alkyl portion has between 1 and 10 carbon atoms.

10. The complex of claim 1 wherein $R_3$ and $R_4$, taken together are cycloalkyl-1,2-diamino, have between about 3 and 7 carbon atoms.

11. The complex of claim 1 wherein $R_1$ and $R_2$, linked together, are a dicarboxylato of the formula:

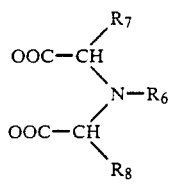

wherein $R_6$ is alkyl having between about 10 and 20 carbon atoms and $R_7$ and $R_8$ are each hydrogen or an alkyl having between about 1 and 5 carbon atoms.

12. The complex of claim 11 wherein $R_7$ and $R_8$ are each hydrogen.

13. The complex of claim 11 wherein the cycloalkyl-1,2-diamino is 1,2-diaminocyclohexane.

14. The complex of claim 13 wherein the 1,2-diaminocyclohexane is defined further as being trans-R,R1,2-diaminocyclohexane or trans-S,S-1,2-diaminocyclohexane.

15. The complex of claim 14 wherein $R_6$ is defined further as being decyl.

16. The complex of claim 14 wherein $R_6$ is decyl, $R_7$ and $R_8$ are hydrogen, and the dicarboxylato is cis.

17. The complex of claim 11 wherein $R_7$ and $R_8$ are hydrogen, and the dicarboxylato is cis.

18. The complex of claim 11 wherein the dicarboxylato is cis.

19. The complex of claim 13 wherein the 1,2-diaminocyclohexane is in the R,R conformation.

20. The complex of claim 1 wherein $R_5$ is hydrogen.

21. The complex of claim 20 wherein $R_1$ and $R_2$ are each an alkylcarboxylato.

22. The complex of claim 1 wherein $R_1$ and $R_2$ are cis.

23. The complex of claim 1 wherein $R_3$ and $R_4$ are linked and are alkyl-1,2-diamino having 2 to 12 carbon atoms.

24. The complex of claim 23 wherein the alkyl is ethyl.

25. The complex of claim 24 wherein $R_1$ and $R_2$ are alkylcarboxylato.

26. The complex of claim 1, wherein $R_1$ and $R_2$ are neo-decanoato of the formula

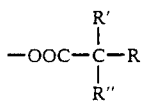

where two of R, R', R" are methyl, ethyl, or propyl.

27. The complex of claim 1, where $R_3$ and $R_4$ are jointly trans-R,R-diaminocyclohexane.

28. The complex of claim 1, where $R_3$ and $R_4$ are jointly trans-S,S-diaminocyclohexane.

29. The complex of claim 1, where $R_1$ and $R_2$ are neo-decanoato of the formula

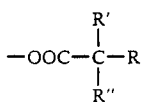

where two of R, R', and R" are methyl, ethyl, or propyl, and where $R_3$ and $R_4$ are jointly a ligand selected from the group consisting of trans-R,R-diaminocyclohexane and trans-S,S-diaminocyclohexane.

30. The complex of claim 1 wherein $R_1$ and $R_2$ are alkylcarboxylato having between about 5 and 20 carbon atoms.

31. The complex of claim 30 wherein $R_1$ and $R_2$ are branched chain alkylcarboxylato.

32. The complex of claim 31 wherein $R_1$ and $R_2$ are branched chain alkylcarboxylato having n carbon atoms, and having the formula:

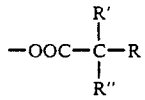

wherein two of R, R' and R" are each methyl, ethyl, or propyl, and the sum of the carbon atoms of R, R', and R" is n-2.

33. The complex of claim 32 wherein n is 10.

34. The complex of claim 32 wherein n is 5 and R, R', and R" are each methyl.

35. The complex of claim 10 wherein the cycloalkyl-1,2-diamino is cyclohexyl-1,2-diamino.

36. The complex of claim 35 wherein $R_1$ and $R_2$ are alkylcarboxylato having between about 5 and 20 carbon atoms.

37. The complex of claim 36 wherein $R_1$ and $R_2$ are branched chain alkylcarboxylato.

38. The complex of claim 37 wherein $R_1$ and $R_2$ are branched chain alkylcarboxylato having n carbon atoms, and having the formula:

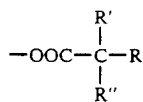
wherein two of R, R' and R" are each methyl, ethyl, or propyl, and the sum of the carbon atoms of R, R', and R" is n-2.
39. The complex of claim 38 wherein n is 10.
40. The complex of claim 38 wherein n is 5 and R, R', and R" are each methyl.
* * * * *

UNITED STATES PATENT AND TRADEMARK OFFICE
CERTIFICATE OF CORRECTION

PATENT NO. : 5,041,581

DATED : August 20, 1991

INVENTOR(S) : Abdul R. Khokhar, et al.

It is certified that error appears in the above-identified patent and that said Letters Patent are hereby corrected as shown below:

At column 2, line 5, after the word "to" should be inserted --be--.

At column 2, line 64, after "thereof" a period should be inserted.

At column 6, line 18, after "(100%)" a period should be inserted.

At column 6, line 43, after "satisfactory" a period should be added.

At column 14, line 34, after "($ID_{50}$)" a period should be added.

At column 15, line 65, "shown" should read --show--.

At column 18, line 29, "L-P" should read --L-PT--.

In claim 1, at column 23, line 1, "carobylato" should read --carboxylato--.

In claim 1, at column 23, line 3, "dicarboxyl to" should read --dicarboxylato--.

UNITED STATES PATENT AND TRADEMARK OFFICE
CERTIFICATE OF CORRECTION

PATENT NO. : 5,041,581

DATED : August 20, 1991

INVENTOR(S) : Abdul R. Khokhar, et al.

It is certified that error appears in the above-identified patent and that said Letters Patent are hereby corrected as shown below:

In claim 1, at column 23, line 5, after "formula:" should be inserted the formula

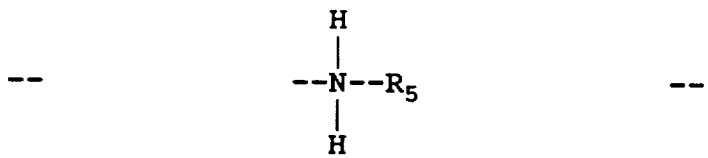

In claim 1, at column 23, line 6, "alky" should read --alkyl--.

In claim 1, at column 23, line 13, "3" should read --2--.

In claim 4, at column 23, line 22, after "5 and 20" should be inserted --carbon--.

In claim 6, at column 23, line 25, "an" should read --a--.

In claim 8, at column 23, line 31, after "between" should be inserted --about--.

In claim 9, at column 23, line 33, after "between" should be inserted --about--.

UNITED STATES PATENT AND TRADEMARK OFFICE
CERTIFICATE OF CORRECTION

PATENT NO. : 5,041,581

DATED : August 20, 1991

INVENTOR(S) : Abdul R. Khokhar, et al.

It is certified that error appears in the above-identified patent and that said Letters Patent are hereby corrected as shown below:

In claim 14, at column 23, line 57, after "R,R" and before "1,2-diaminocyclohexane" should be inserted a hyphen.

In claim 26, at column 24, line 21, after "R'," and before "R''" should be inserted --and--.

Signed and Sealed this

Sixteenth Day of March, 1993

Attest:

STEPHEN G. KUNIN

Attesting Officer

Acting Commissioner of Patents and Trademarks